United States Patent [19]

Kaspari et al.

[11] 4,058,117

[45] Nov. 15, 1977

[54] BLOOD PRESSURE MEASURING APPARATUS

[75] Inventors: William J. Kaspari, Portola Valley; Herman Wong, Los Altos Hills; Joseph L. Kirch, Hollister, all of Calif.

[73] Assignee: Palo Alto Research Associates, Portola Valley, Calif.

[21] Appl. No.: 623,242

[22] Filed: Oct. 17, 1975

[51] Int. Cl.² ............................................. A61B 5/02
[52] U.S. Cl. .......................... 128/2.05 A; 128/2.05 C; 128/2.05 M
[58] Field of Search ..................... 128/2.05 A, 2.05 C, 128/2.05 G, 2.05 M, 2.05 Q, 327

[56] References Cited

U.S. PATENT DOCUMENTS

| | | | |
|---|---|---|---|
| 2,405,265 | 8/1946 | McAlpine | 128/2.05 G |
| 2,869,536 | 1/1959 | Speelman | 128/2.05 G |
| 3,258,009 | 6/1966 | London | 128/2.05 C |
| 3,450,131 | 6/1969 | Vogt | 128/2.05 A |
| 3,533,401 | 10/1970 | Streu | 128/2.05 A |
| 3,552,381 | 1/1971 | Burns | 128/2.05 A |
| 3,814,083 | 6/1974 | Fletcher | 128/2.05 A |
| 3,893,452 | 7/1975 | Birnbaum | 128/2.05 A |
| 3,896,791 | 7/1975 | Ono | 128/2.05 G |
| 3,905,354 | 9/1975 | Lichowsky | 128/2.05 M |
| 3,906,937 | 9/1975 | Aronson | 128/2.05 C |
| 3,935,984 | 2/1976 | Lichowsky et al. | 128/2.05 M |

FOREIGN PATENT DOCUMENTS

| | | | |
|---|---|---|---|
| 2,336,974 | 2/1975 | Germany | 128/2.05 C |
| 978,074 | 12/1964 | United Kingdom | 128/2.05 M |

OTHER PUBLICATIONS

Schulze et al., "A system . . . Blood Pressures," Southwestern Inst. of Electrical & Electronics Eng. Conf. Record, Apr. 1968, 5 pages.

*Primary Examiner*—Robert W. Michell
*Assistant Examiner*—Lee S. Cohen

[57] ABSTRACT

A fully automatic, non-invasive, digitally-controlled blood pressure measuring apparatus is described with LED displays for displaying systolic and diastolic blood pressure levels, an inflatable cuff for occluding an artery, a pump for inflating the cuff, a cuff-mounted sensor for detecting Korotkoff sounds, adjustable gain-amplifying apparatus for maintaining linearity of the Korotkoff sound levels over a wide range of human individuals, circuits for automatically determining systolic and diastolic pressure levels and pressure release apparatus for preventing overinflation of the cuff.

6 Claims, 8 Drawing Figures

BLOOD PRESSURE MEASURING APPARATUS

BACKGROUND OF THE INVENTION

The present invention relates to blood pressure measuring apparatus in general and in particular to a fully automatic, non-invasive, digitally-controlled apparatus with digital registers and LED's for providing a readout of systolic and diastolic blood pressure levels.

Typically, the systolic blood pressure is defined as that pressure in the vascular system which exists when the heart is active — i.e., pumping. It is determined as corresponding to the pressure in a cuff required to effect approximately total occlusion of the brachial artery. The diastolic pressure, on the other hand, is defined as that pressure in the vascular system existing when the artery returns to its non-occluded shape. It is determined as corresponding to the pressure in a cuff when an artery becomes approximately fully patent. Whether an artery is occluded or patent is determined by the sounds or lack of sounds created by the blood coursing through the artery. These sounds, commonly called Korotkoff sounds or pulses, are measurable as the artery is partially occluded.

In the course of taking a blood pressure measurement, the Korotkoff sounds are found to vary in amplitude and frequency. Moreover, the amplitude and frequency of the sounds may, and usually do, vary from individual to individual. Also, as is found when using a stethoscope, it is quite difficult to detect quantitatively a change in the sound intensity — i.e., amplitude. Noise is frequently prominent and partly to blame for this difficulty.

For these reasons, among others, previous proposals for automatic blood pressure measuring apparatus have generally involved various types of audio-frequency filtering. Filtering, heretofore, it would appear, has been considered the most effective way to eliminate audio-frequency noise and the effects of noise on the blood pressure measurements.

The above described prior known methods and apparatus as well as others employing low-frequency sound transmitters and receivers, however, are considerably removed from the conventional method of utilizing systolic and Phase IV and V diastolic readings. They are, in contrast to the present invention, concerned principally with sound frequencies as distinguished from sound intensities. It is the latter with which physicians are most familiar and which are employed when taking blood pressures in a conventional manner. Blood pressure readings which are taken using the same criteria — e.g., sound intensities — as commonly used by physicians are much more meaningful to a wider number of physicians and consequently more meaningful to the public at large. This is of particular importance because it is to the latter group that the present invention is especially directed.

SUMMARY OF THE INVENTION

In view of the foregoing, a principal object of the present invention is a fully automatic blood pressure measuring apparatus.

Another object is a blood pressure measuring apparatus having self-adjusting circuits for automatically measuring the blood pressure of a wide range of human individuals.

Another object is a blood pressure measuring apparatus which, while being fully automatic, employs substantially the same criteria for measuring systolic and diastolic blood pressure levels as employed by physicians — namely, Korotkoff first, fourth and fifth phase sound levels.

Still another object is a blood pressure measuring apparatus which has a digital readout of systolic and diastolic blood pressure levels.

Still another object of the present invention is a blood pressure measuring apparatus which is fully automatic and is usable, accurate, and reliable without the intervention of trained personnel.

Still another object is a blood pressure measuring apparatus which may be operated entirely by the subject whose blood pressure is being measured.

A feature of one or more of the above objects is an inflatable cuff which is adapted for fitting about a subject's limb — e.g., an arm. A pump means is employed for inflating the cuff at a predetermined rate, as of 10 mm Hg/second. Inflating the cuff provides for occluding an artery, typically the brachial artery. During the inflation of the cuff, Korotkoff sounds created by the occlusion of the artery are detected by means of a sensor in the cuff, amplified by an audio amplifier and employed for adjusting the gain of the amplifier. The gain adjustment for the amplifier during "pump-up" provides for linear amplification of the Korotkoff sounds during the subsequent blood pressure measuring portion of the cycle.

When a total occlusion of the brachial artery is achieved as determined by a reduction of the amplitude of the Korotkoff sounds to a predetermined level, further inflation of the cuff is automatically terminated, a noise threshold level is set in the Korotkoff sound portion of the measuring circuits and deflation of the cuff is begun at a controlled manually-adjustable rate.

As the cuff automatically deflates, the first Korotkoff sound pulse having a predetermined amplitude is detected and employed to display a signal proportional to the then current cuff pressure level in a digital display designated systolic pressure. Thereafter, two methods are provided for measuring diastolic pressure. In one, subsequent pulses are held in current pulse and preceding pulses sample and hold circuits. The amplitude of a current pulse is compared with the amplitude of the highest of the preceding pulses and, when found to be less than a predetermined fraction of the amplitude of the highest of the preceding pulses, causes a signal proportional to the then current cuff pressure to be displayed in a register designated diastolic pressure and the test is terminated. In another, the subsequent pulses are detected until their amplitude becomes less than a predetermined amplitude. At that point, cuff pressure is read out as the diastolic pressure. The two methods described are called, respectively, Fourth and Fifth Phase diastolic pressure levels.

Various other features of the present invention provide for safety in use, noise compensation, compensation as required for different individuals and the rejection of invalid test results.

DESCRIPTION OF THE DRAWINGS

The above and other objects, features and advantages of the present invention will be apparent from the detailed description which follows, and the accompanying drawings in which.

DETAILED DESCRIPTION

Figures 1, 2:
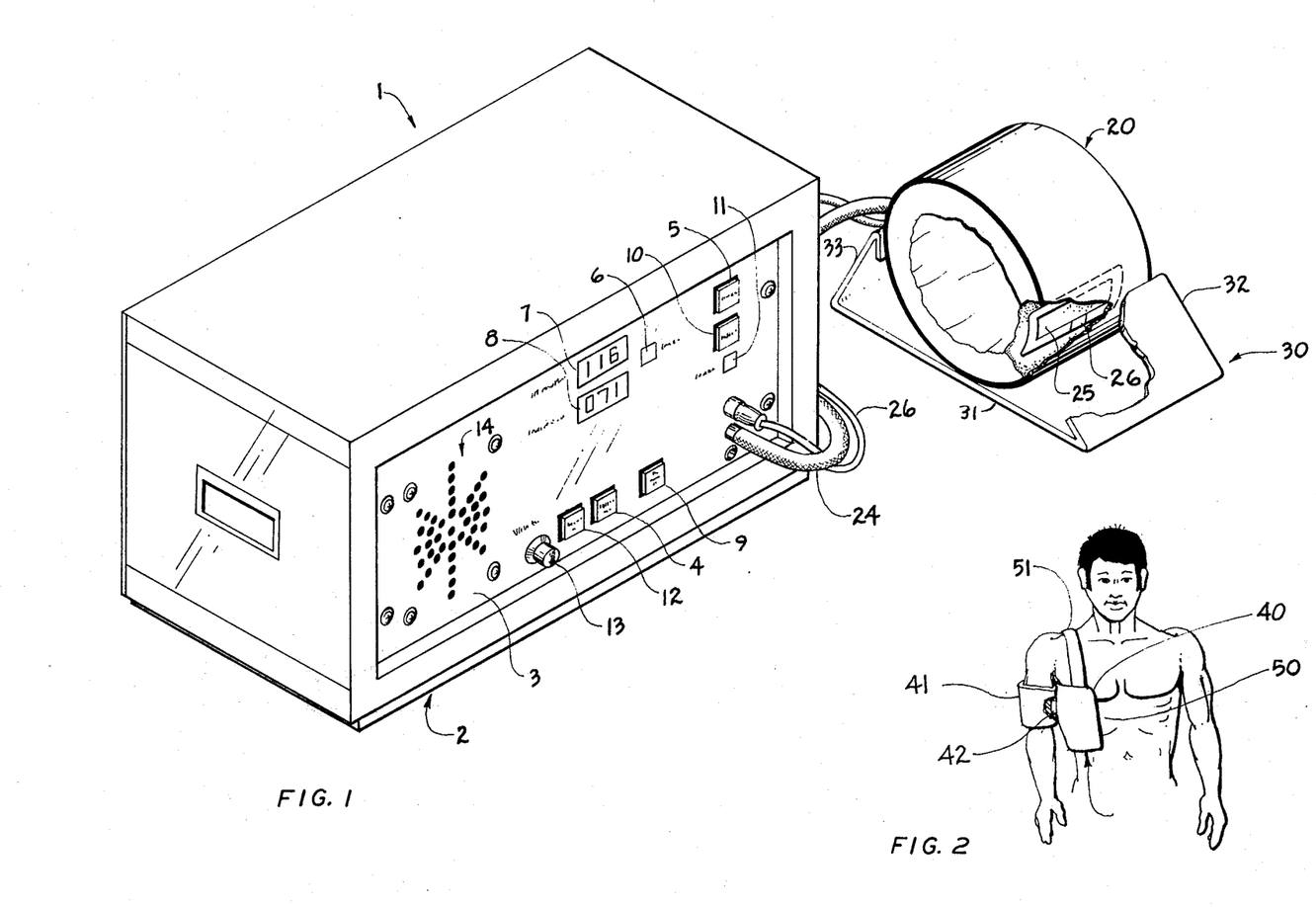
FIG. 1 is a perspective view of an apparatus according to the present invention.
FIG. 2 is an alternative embodiment of a cuff assembly of the present invention.

Referring to FIG. 1, there is provided, in accordance with the present invention, a blood pressure measuring apparatus 1 comprising an electronic assembly 2 having a front panel 3.

In panel 3, there is provided a "power-on" switch 4 and a "ready" light 5. Switch 4 is operable for applying power to the apparatus and the "ready" light 5 is illuminated when the apparatus is ready to be used. To the left of the light 5 is a "start" switch 6. Switch 6 is operated for starting a blood pressure measuring cycle of operation after the "ready" light 5 is illuminated. To the left of the "start" switch 6 is a pair of registers 7 and 8 designated, respectively, systolic and diastolic. Registers 7 and 8 comprise light-emitting diodes and are employed for providing a digital readout of systolic and diastolic blood pressure levels at the end of the test cycle. Below "start" switch 6 is a switch 9 designated IV/V. Switch 9 is employed for selecting between Phase IV and Phase V diastolic pressure level readings. Additionally, there is provided below the "ready" light 5, a "Repeat Test" light 10 and a "Release" switch 11. Light 10 is illuminated when, for any reason, the apparatus does not cycle through its normal sequence of operations and there is a failure to provide a readout in the registers 7 and 8. As options for those desiring to listen to the heart beat and blood flow as is normally done with a stethoscope by a physician when measuring blood pressure in a conventional manner, there is provided a "sound on" switch 12, volume control 13 and speaker indicated at 14 and located behind the perforations in the panel 3.

To the right of electronic assembly 2 there is shown an inflatable cuff assembly 20. In assembly 20 there is provided an annular cuff member 21. In the interior of cuff member 21 there is provided an inflatable bladder 23. Bladder 23 is airtight and extends uniformly about the interior of the cuff member 21 and is typically enclosed or otherwise covered by an elastic fabric. Coupled between the assembly 2 and bladder 23 is an air tube or hose 24. Tube 24 is employed for inflating the bladder and measuring its internal pressure. As will be apparent, it is this pressure which is used as a measure of blood pressure.

Located adjacent to the bladder 23 on an interior surface of the cuff member 21 is an acoustically-responsive sensor 25. In sensor 25 there is provided an acoustically-responsive diaphragm which is adapted to vibrate in response to an acoustic input for generating a corresponding acoustic signal in a tube 26. In a preferred embodiment of the present invention, the signal thus generated is transmitted by the acoustic tube 26 to the assembly 2 wherein it is converted to an electrical signal. In another embodiment, the sensor 25 may be replaced by a transducer for generating an electrical signal directly at the cuff.

Proper placement of the cuff member 21 and, in particular, the sensor 25 on a subject's arm is important for obtaining good blood pressure measurements. As will be apparent, the sensor must be placed in the vicinity of the brachial artery and preferably as close thereto as possible. The closer the sensor is to the artery, the better will be the signal-to-noise ratio.

To facilitate proper placement of the cuff member 21, the cuff member 21 is supported in a U-shaped bracket 30. In bracket 30 there is a base member 31. Extending upwardly and inwardly from opposite ends of the base member 31 is a pair of end members 32 and 33. Members 32 and 33, in cooperation with base member 31, hold the cuff member 21 in a fixed position so that a subject may simply insert his arm through the center of the cuff and the sensor 25 will be in the proper location relative to the subject's brachial artery.

Referring to FIG. 2, there is provided an alternative cuff assembly 40 for use with the electronic assembly 2 of FIG. 1. In assembly 40, there is provided a cuff member 41. In member 41 there is provided an acoustically-responsive sensing means 42 and a bladder (not shown) which are identical to the corresponding elements in the cuff 20 of FIG. 1.

To the right of cuff member 41 is a chest plate 50. Plate 50 is made to conform comfortably to the surface of the subject's body beneath the armpit. It extends from the chest area to the back area. Attached to the top of the plate at the front and the back is a shoulder strap 51. Strap 51 is provided for suspending the plate from a subject's shoulder. The cuff member 41 is attached to the plate 50 in any suitable manner for holding the cuff member 41 and sensor 42 in a proper position relative to the subject's brachial artery. A means (not shown), such as tubes identical to tubes 24 and 26 of FIG. 1, are typically employed for coupling the cuff member 41 to the assembly 2. The plate 50 may be made of a formed rigid material or a weighted pad or the like.

Figure 3A:
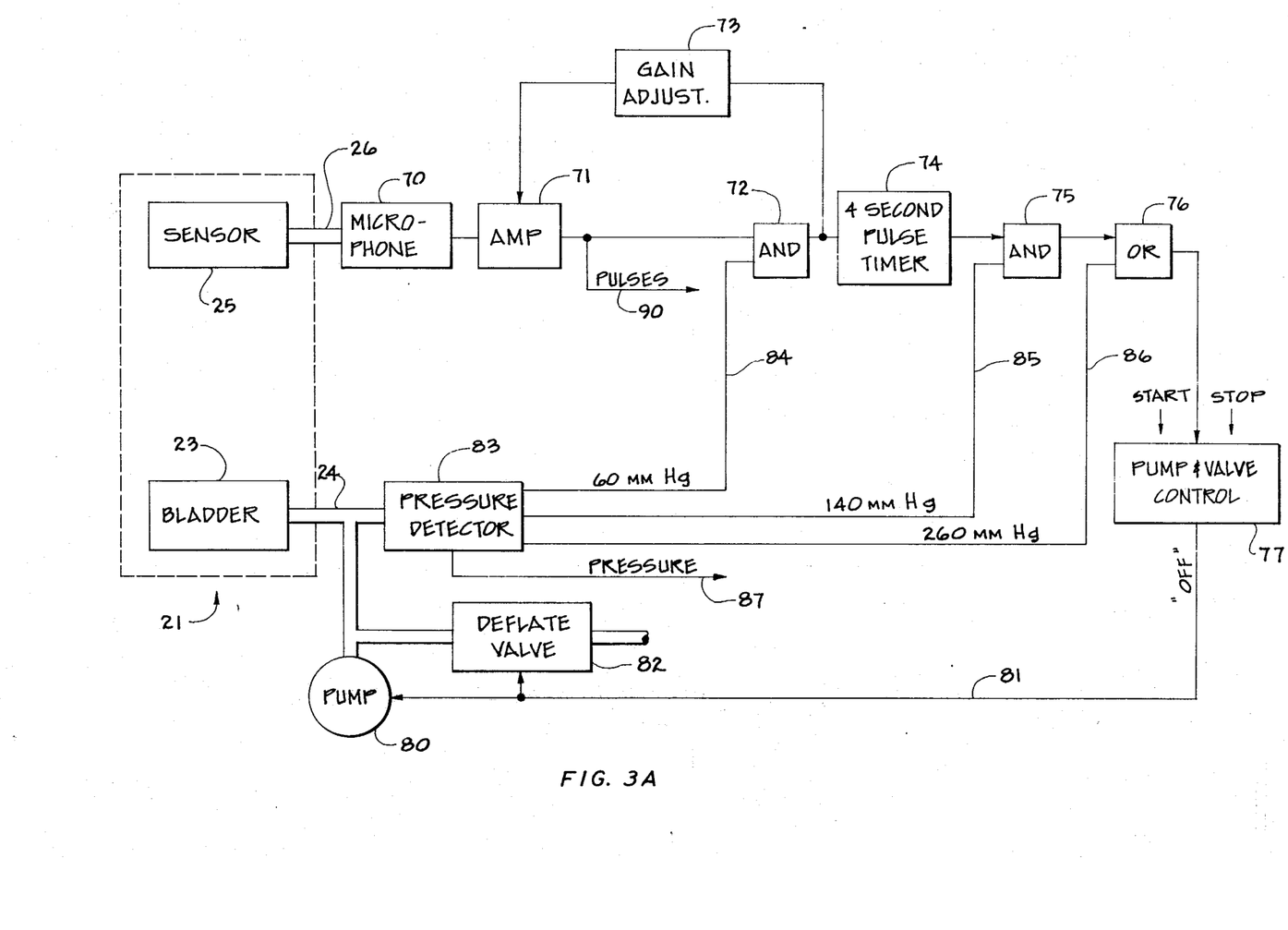
FIGS. 3A and 3B are block diagrams of the apparatus of FIG. 1.
Figure 3B:
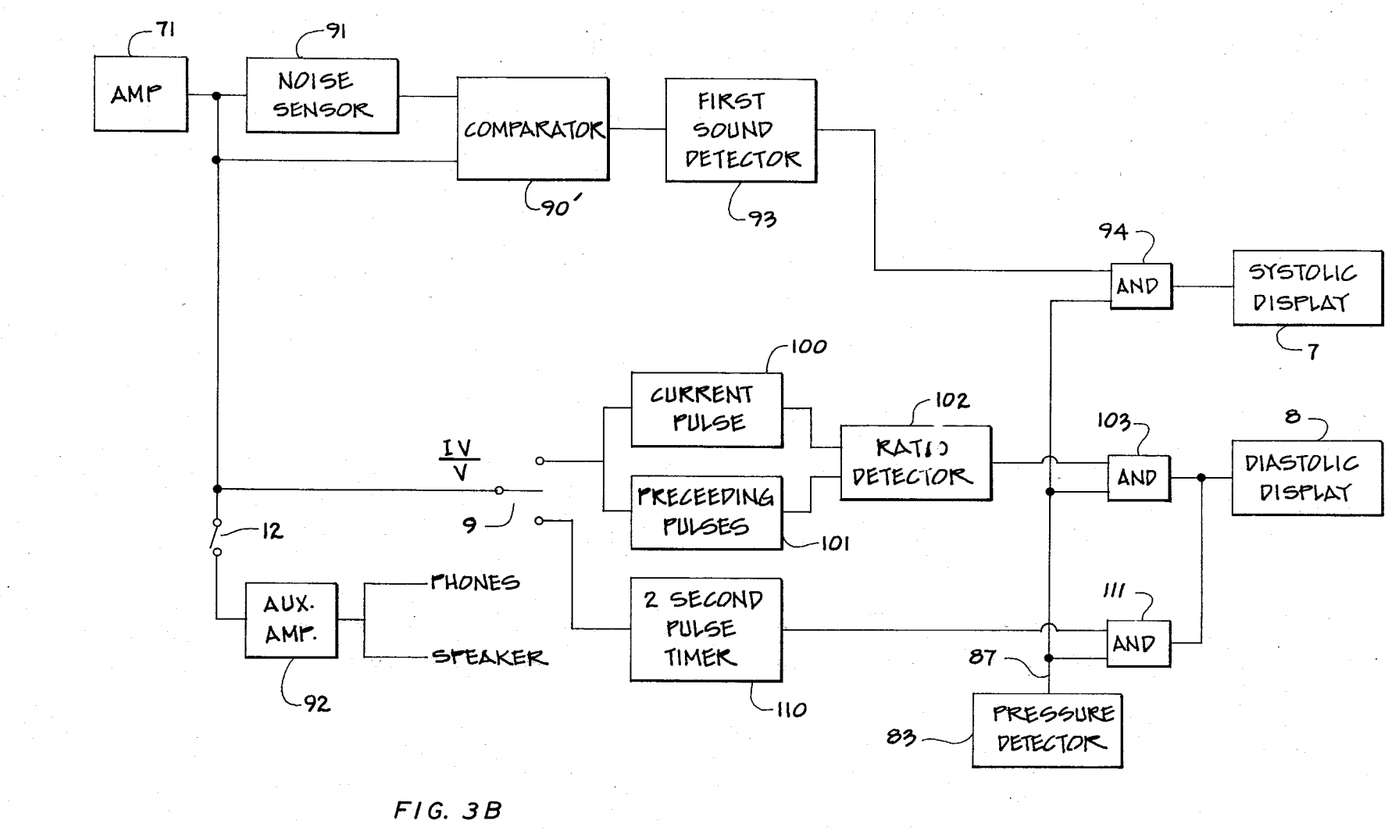
Figure 4:
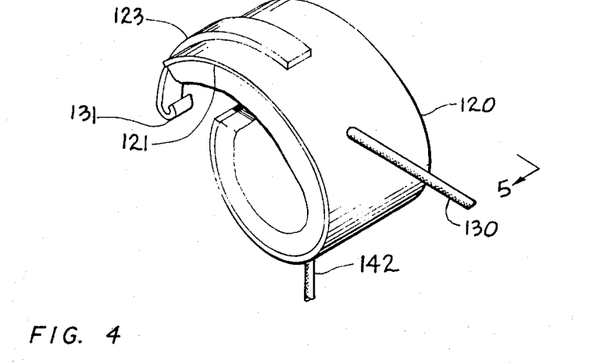
FIG. 4 is a perspective view of another embodiment of a cuff assembly according to the present invention.

In FIGS. 3A and 3B, the apparatus of FIG. 1 is shown in a pair of block diagrams. Two diagrams are used for convenience and clarity of illustration. FIG. 3A shows the part of the apparatus used during cuff inflation and pre-setting of certain ones of the circuits, and FIG. 3B shows the part of the apparatus used during cuff deflation and the taking of the pressure measurements.

Referring to FIG. 3A, the cuff member 21 is represented therein by a rectangle of broken lines. In the upper part of the rectangle is shown the sensor 25. Sensor 25 is coupled to a microphone 70 by the air tube 26. Microphone 70 is provided for converting the acoustic signals generated by the sensor 25 and transmitted thereto via tube 26 to corresponding electrical signals. Coupled to the output of microphone 70 is an audio-frequency amplifier circuit means 71. Circuit 71 is provided for amplifying the output of the microphone 70. Coupled to the output of amplifying circuit 71 there is provided an AND circuit 72. Coupled to the AND circuit 72 is a gain-adjusting circuit 73 and a four-second pulse timing circuit 74.

The gain-adjusting circuit 73 is coupled to the amplifying circuit 71 for reducing the gain of the amplifying circuit when its input signals from the microphone 70 exceed a predetermined threshold level. The four-second timing circuit 74, also coupled to AND circuit 72, is provided for providing an output signal at any time there is no input signal thereto for a period of four seconds.

Coupled in series to the output of timing circuit 74 is an AND circuit 75, an OR circuit 76 and a pump and valve control circuit 77.

Below the sensor 25 in FIG. 3A, is shown the bladder 23. Bladder 23 is coupled, by means of the air tube 24, to an air pump 80. Pump 80 is coupled to pump and valve control circuit 77 by a line 81, and is provided for inflating the bladder 23 at a predetermined rate — e.g., 10 mm Hg/second. Coupled to bladder 23 by means of the air tube 24 and to control line 81 is a cuff deflation valve 82. Valve 82 is provided for deflating the cuff 21 at a predetermined rate — e.g., 3 mm Hg/second. In addition to pump 80 and valve 82, there is provided a pressure detection circuit 83. Pressure detection circuit 83 is coupled to bladder 23 by the air tube 24. At the output of circuit 83, there is provided a plurality of control lines 84, 85 and 86 and a pressure level output line 87. Line 84 is coupled to the AND circuit 72 for enabling that circuit when the cuff pressure reaches a predetermined level — e.g., 60 mm Hg. Line 85 is coupled to the AND circuit 75 for enabling that circuit when the cuff pressure reaches a second predetermined level — e.g., 140 mm Hg. Line 86 is coupled to OR circuit 76 for shutting off the pump 80 whenever the cuff pressure reaches a third predetermined level — e.g., 260 mm Hg. The third level control is provided as a safety feature in the event of a system malfunction or the like. The line 87, designated as the pressure level output line, is provided for providing cuff pressure level information to the registers 7 and 8, as will be described further with respect to FIG. 3B.

Referring to FIG. 3B, the amplifying circuit means 71 is coupled to a comparator circuit 90', a noise level sensor 91, the Phase IV/Phase V switch 9 and an auxiliary audio amplifier 92. Coupled in series with the comparator circuit 90' is a first sound detector 93, an AND circuit 94 and the systolic display register 7. The switch 9 has at least two output contacts and a wiper. The amplifier 71 is coupled to the wiper. Coupled in parallel to one of the contacts of the switch 9 is a current pulse sample and hold circuit 100 and a preceding pulses sample and hold circuit 101. Coupled in series to the output of the circuits 100 and 101 is a ratio detection circuit 102, an AND circuit 103 and the diastolic display register 8. Coupled in series to another of the contacts of the switch 9 is a two-second pulse timing circuit 110, an AND circuit 111 and the diastolic display register 8. Coupled to each of the AND circuits 94, 103 and 111 is the line 87 from the pressure detector circuit 83. Coupled to auxiliary amplifier 92 is the speaker 14 and, optionally, headphones.

In practice, a subject desiring to measure his or her blood pressure, inserts an arm through the cuff 21 and operates the "power on" switch 4. In commercial use, operation of switch 4 may be done by means of a coin-operated mechanism. As soon as the "ready" light 5 is illuminated, the machine is ready. Upon operation of the "start" switch 6, the cuff 21 begins to inflate at the rate of 10 mm Hg/second. This rate is not critical and may be varied. As the cuff inflates and begins to occlude the brachial artery, Korotkoff sounds or pulses are created. In some individuals, the intensity of the Korotkoff sounds may be quite high. In others, the sound intensity may be very low. When the sound intensity exceeds a predetermined threshold level, the gain of the amplifier 71 is reduced by the gain-adjusting circuit 73. This insures that the output of the amplifier will be linear over a wide range of individuals having high and low intensity Korotkoff pulse profiles. However, to avoid reducing the gain prematurely, as might occur if sensor 25 picked up high amplitude noise during the initial stages of cuff inflation, when the cuff is loose fitting and subject to movement, the AND circuit 72 is not enabled until the cuff pressure reaches 60 mm Hg and a corresponding control signal is generated on line 84.

Once started, the pump 80 will continue to inflate cuff 21 until the Korotkoff pulses cease. The pulses cease when the blood flow has stopped in the artery. To determine when the pulses have stopped, the pulses are fed to the four-second pulse timing circuit 74. The circuit 74 outputs a pulse or other signal for turning off the pump 80 whenever there has been a lapse of more than four seconds between input pulses. Since pulse beats occur on the average at the rate of 50 to 70 beats per minute, or about one beat a second, the detecting of the absence of beats for four seconds is a reliable method for determining when the pulses have ceased. In some extreme cases, such as a person with very high diastolic pressure level, these pulses may not occur until very high pressures — e.g., 140 mm Hg — are reached. Accordingly, AND circuit 75 is disabled until the cuff pressure reaches 140 mm Hg and a control signal is generated on the line 85 for enabling the circuit. Once the circuit is enabled, an output from the circuit 74 will pass through to operate control 77. It should be noted, however, that since timer 74 does not generate a signal until four seconds after a previous pulse, the ultimate cuff pressure will typically be 40 mm Hg higher than the systolic pressure.

As a precaution against over-inflation of the cuff as might occur, for example, when a broken wire or the like generates sufficient noise to prevent the generation of an "off" signal by the timing circuit 74, there is provided the control signal on the line 86. The control signal on the line 86 is generated whenever the cuff pressure reaches 260 mm Hg.

The control signal for turning off the pump 80, however generated, also operates the valve means 82 for initiating deflation of the cuff at an adjustable predetermined rate as of 3 mm Hg/second.

By the time the pump 80 is turned off and valve 82 opened, the gain of the amplifier is set to provide the linear output during the next succeeding deflation portion of the operating cycle. Also, by this time, the switch 9 will have been set to either the Phase IV or the Phase V position by the operator.

It will be recalled that the pump 80 continues to operate for about four seconds after the systolic pulse — i.e., the Korotkoff pulses — cease. Because of this, there is a period of time between initiation of deflation and the time at which the systolic pulse occurs. This period is used for making a noise compensation adjustment. Within this period, the noise level sensor 94 detects the noise level on the output of the amplifier 71 and sets the threshold of the comparator 90'. This threshold may vary over a predetermined range depending on the noise level. The first sound or pulse exceeding the threshold after the threshold has been set for the comparator 90' will generate a signal in the circuit 93 enabling the AND circuit 94, permitting the then current cuff pressure from pressure detector 83 to be displayed in register 7. Thereafter, AND circuit 94 is disabled holding the systolic pressure in register 7.

As the cuff continues to deflate, the output of the amplifying circuit 71 is applied through the switch 9, depending on its position, to either the circuits 100 and 101 or to the two-second pulse-timing circuit 110. If a Phase IV test is desired, the circuits 100 and 101 are used, the circuit 100 samples and holds the amplitude of the current pulses and circuit 101 samples and holds the amplitude of the pulse having the highest amplitude of all of the preceding pulses. These amplitudes are then compared in the ratio detector 102 and, when the amplitude of the current pulse is a predetermined fraction, such as 50% of the amplitude of the highest of the preceding pulses, a control signal is generated by the detector 102 enabling the AND gate 103, permitting the display of the then current cuff pressure in the diastolic register 8.

When the Phase V test is desired, the output of the amplifying circuit 71 is fed to the two-second pulse timing circuit 110. After the absence of an input for two seconds, the circuit 110 generates a signal on its output enabling the gate circuit 111, permitting the display in register 8 of the cuff pressure at the time of the last pulse detected.

Whenever it is desired to listen to the Korotkoff sounds, switch 12 may be operated, coupling the amplifier 92 and speaker 14 to the amplifier 71.

Referring to FIGS. 5-8, there is shown an alternative inflatable cuff 120 for use with the apparatus of FIG. 1. In cuff 120, there is provided a spring member 121. Spring member 121 is made from a rectangular piece of resilient material, such as spring steel which is formed in a spiral fashion so as tend to close upon itself when its ends are spread apart and released. Attached to the interior surface of member 121 is an inflatable bladder 122. Bladder 122 extends substantially over the entire interior surface of member 121. Coupled to the bladder is an air hose 130. Hose 130 is provided for coupling the bladder to the pump 80 and corresponds to the hose 24 of FIG. 1. Fitted to and extending from the outer end of member 121 is a hook member 123 having an inwardly directed hook portion 131. Fitted at spaced points from the inner end of the member 121 is a plurality of catch members 124. Each of catch members 124 comprises a bracket 125 having a pair of rolled strap portions 126 and 127 for retaining a pin 128. Each of the members 124 is attached to the spring member 121 as by rivets or the like.

Figure 5:
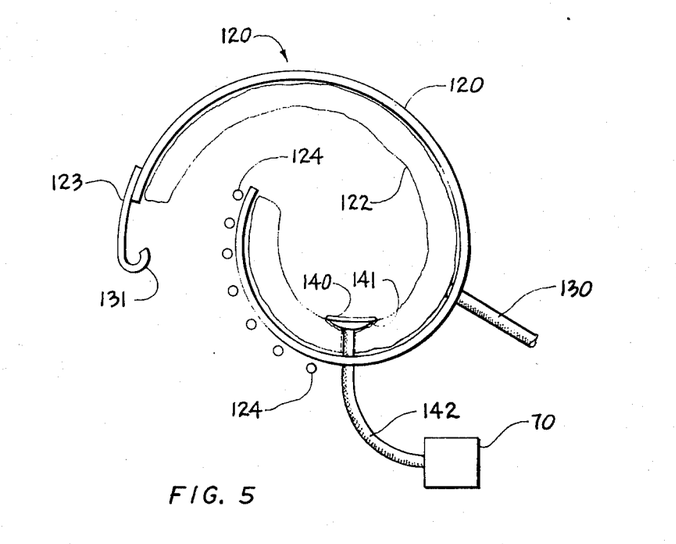
FIG. 5 is a cross-sectional view taken along lines 5—5 of FIG. 4
Figure 6:
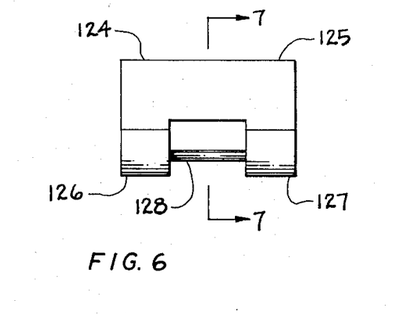
FIG. 6 is a catch member on the cuff of FIG. 5.
Figure 7:
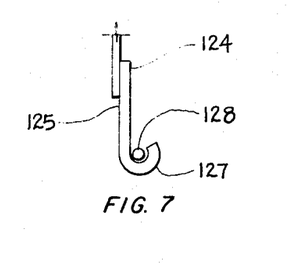
FIG. 7 is a cross-sectional view taken along lines 7—7 of FIG. 6.

In the interior of the cuff 120, there is provided an acoustically responsive diaphragm 140. Diaphragm 140 is substantially identical to a conventional stethoscope diaphragm and is mounted on the bladder 122 in a position to overlay the brachial artery when the cuff is put on. For increasing pressure on the diaphragm to force the diaphragm tightly against the arm over the brachial artery, the diaphragm is preferably mounted to the bladder with an intermediate piece of sponge or the like 141. Coupled to the rear of diaphragm 140 is an acoustic tube 142. Tube 142 is provided for coupling the tube ana transmitting acoustic waves generated by the diaphragm to the microphone 70 in the apparatus of FIG. 1.

The cuff 120 is an important feature of the present invention in that it permits single-handed appliction of the cuff. Moreover, the expandable and elastic nature of the cuff permits fitting to a wide range of arm sizes.

In use, the cuff, when put on, spreads comfortably to fit the arm. When the diaphragm 140 is positioned over the brachial artery, the hook 123 is simply caused to engage the nearest pin 128 in a closing direction to secure the cuff and prevent its opening during inflation. Because the cuff tends to close itself, the hooking of hook 123 can be done with one hand by the subject taking the test.

A further important feature of the present invention is the use of the stethoscope type diaphragm 140 as distinguished from an electrical transducer in the cuff.

Being similar to a stethoscope diaphragm, diaphragm 140 provides an output which is very similar to the sounds heard by a physician using a stethoscope during a conventional blood pressure measurement. Accordingly, there is possible a very close correspondence between the measurements taken with the present invention and those taken by a physician using a conventional stethoscope. This can be very helpful to a physician who is considering the significance of the measurements taken with the apparatus in that he or she is in a better position to relate the measurements to their own personal experiences.

A preferred embodiment of the invention has been described herein. It is understood, however, that the various pressure threshold levels described may be changed and a variety of changes made in the details of the apparatus and their arrangement may also be made within the spirit and scope of the present invention — e.g., the Phase IV determination can be made by comparing the current pulse to a predetermined percentage of the average level of the preceding pulses. Accordingly, it is intended that the scope of the invention should not be restricted to the embodiment described but rather be determined by reference to the claims hereinafter provided.

What is claimed is:

1. A blood pressure measuring apparatus comprising:
 an inflatable cuff adapted to occlude an artery when inflated;
 means for inflating said cuff means from a cuff condition of non-inflation to a cuff pressure sufficient to occlude an artery without interruption;
 means mounted in said cuff means for detecting sounds created when said cuff means occludes an artery;
 means coupled to said detecting means for amplifying said sounds;
 means responsive to said amplifying means during said inflation of said cuff means for automatically reducing the gain of said amplifying means when said sounds exceed a predetermined amplitude during said uninterrupted inflating of said cuff means, said gain-reducing means comprising means for reducing said gain of said amplifying means only when said cuff means has been inflated to at least a first predetermined pressure;
 means responsive to a cessation of said sounds for a predetermined period during said uninterrupted inflating of said cuff means for automatically stopping said inflating of said cuff means;
 means for deflating said cuff means automatically after said stopping of said inflating of said cuff means;
 means for detecting the first sound having a predetermined amplitude following the initiation of said deflating of said cuff means;
 means responsive to said detecting of said first sound for displaying a first cuff pressure, as a measure of systolic blood pressure in said artery; and
 means responsive to subsequent sounds during continued deflating of said cuff means for automatically displaying a second cuff pressure as a measure of diastolic blood pressure when a first one of said subsequent sounds has an amplitude which is less than a predetermined amplitude.

2. An apparatus according to claim 1 wherein said stopping means for stopping said inflating of said cuff means comprises means for stopping said inflating means upon a cessation of said sounds for said predetermined period only when said cuff means has been inflated to at least a second predetermined pressure.

3. An apparatus according to claim 2 further comprising means for stopping said inflating means even if said sounds have not ceased when said cuff means has been inflated to a third predetermined level.

4. An apparatus according to claim 3 wherein said first predetermined pressure is chosen to prevent noise generated during initial inflating of said cuff means from causing said amplifying means gain reduction, said second predetermined pressure is chosen to prevent premature stopping of said inflating means, and said third predetermined pressure is chosen to prevent overinflation of said cuff means in the event of a malfunction or the like in said apparatus resulting in apparent Korotkoff sounds.

5. An apparatus according to claim 4 wherein said first, said second and said third predetermined pressures are approximately 60 mm Hg, 140 mm Hg and 260 mm Hg.

6. A blood measuring apparatus comprising:
an inflatable cuff means adapted to occlude an artery when inflated;
means for inflating said cuff means from a cuff condition of non-inflation to a cuff pressure sufficient to occlude an artery without interruption;
means mounted in said cuff means for detecting sounds created when said cuff means occludes an artery;
means coupled to said detecting means for amplifying said sounds;
means responsive to said amplifying means during said inflation of said cuff means for automatically reducing the gain of said amplifying means when said sounds exceed a predetermined amplitude during said uninterrupted inflating of said cuff means;
means responsive to a cessation of said sounds for a predetermined period during said uninterrupted inflating of said cuff means for automatically stopping said inflating of said cuff means;
means for deflating said cuff means automatically after said stopping of said inflating of said cuff means;
means for detecting the first sound having a predetermined amplitude following the initiation of said deflating of said cuff means;
means responsive to said detecting of said first sound for displaying a first cuff pressure, as a measure of systolic blood pressure in said artery;
means responsive to subsequent sounds during continued deflating of said cuff means for automatically displaying a second cuff pressure as a measure of diastolic blood pressure when a first one of said subsequent sounds has an amplitude which is less than a predetermined amplitude; and
means for suspending said cuff means from a shoulder, said suspending means including a shoulder strap means a chest plate, and means for mounting said cuff means to said strap means and plate for holding said cuff means mounted sound detecting means in a predetermined position relative to the source of said sounds.

* * * * *

UNITED STATES PATENT OFFICE
CERTIFICATE OF CORRECTION

Patent No. 4,058,117          Dated Nov. 15, 1977

Inventor(s) William J. Kaspari

It is certified that error appears in the above-identified patent and that said Letters Patent are hereby corrected as shown below:

On the cover sheet, in item [75] add the name of inventor -- Lawrence F. Herte, Palo Alto, Calif. --.

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*